United States Patent
Boyd et al.

(10) Patent No.: US 10,258,546 B2
(45) Date of Patent: *Apr. 16, 2019

(54) TOOTH WHITENING STRIP

(75) Inventors: Thomas Boyd, Metuchen, NJ (US); Guofeng Xu, Plainsboro, NJ (US); Richard Adams, Monmouth Junction, NJ (US); Robert Pierce, South Orange, NJ (US); Steven Miller, Skillman, NJ (US); David Viscio, Prescott Valley, AZ (US)

(73) Assignee: Colgate-Palmolive Company, New York, NY (US)

( * ) Notice: Subject to any disclaimer, the term of this patent is extended or adjusted under 35 U.S.C. 154(b) by 54 days.

This patent is subject to a terminal disclaimer.

(21) Appl. No.: 14/344,786

(22) PCT Filed: Sep. 14, 2011

(86) PCT No.: PCT/US2011/051546
§ 371 (c)(1),
(2), (4) Date: Mar. 13, 2014

(87) PCT Pub. No.: WO2013/039495
PCT Pub. Date: Mar. 21, 2013

(65) Prior Publication Data
US 2014/0338688 A1    Nov. 20, 2014

(51) Int. Cl.
| A61K 8/02 | (2006.01) |
| A61K 8/38 | (2006.01) |
| A61K 8/22 | (2006.01) |
| A61Q 11/00 | (2006.01) |
| A61K 8/73 | (2006.01) |
| A61K 8/81 | (2006.01) |

(52) U.S. Cl.
CPC .......... *A61K 8/0245* (2013.01); *A61K 8/0208* (2013.01); *A61K 8/22* (2013.01); *A61K 8/38* (2013.01); *A61K 8/731* (2013.01); *A61K 8/8141* (2013.01); *A61K 8/8147* (2013.01); *A61Q 11/00* (2013.01); *A61K 2800/56* (2013.01); *A61K 2800/87* (2013.01)

(58) Field of Classification Search
None
See application file for complete search history.

(56) References Cited

U.S. PATENT DOCUMENTS

| 5,279,816 A | 1/1994 | Church et al. |
| 5,302,375 A | 4/1994 | Viscio |
| 5,403,549 A | 4/1995 | McNeil et al. |
| 5,746,598 A | 5/1998 | Fischer |
| 5,879,691 A | 3/1999 | Sagel et al. |
| 5,891,453 A | 4/1999 | Sagel et al. |
| 5,894,017 A | 4/1999 | Sagel et al. |
| 5,989,526 A | 11/1999 | Aaslyng et al. |
| 6,136,297 A | 10/2000 | Sagel et al. |
| 6,221,341 B1 | 4/2001 | Montgomery |
| 6,274,122 B1 | 8/2001 | McLaughlin et al. |
| 6,379,653 B1 | 4/2002 | Aaslyng et al. |
| 6,419,906 B1 | 7/2002 | Xu et al. |
| 6,503,485 B1 | 1/2003 | Allred et al. |
| 6,503,486 B2 | 1/2003 | Xu et al. |
| 6,551,579 B2 | 4/2003 | Sagel et al. |
| 6,669,929 B1 | 12/2003 | Boyd et al. |
| 6,682,712 B2 | 1/2004 | Angaiah et al. |
| 6,682,721 B2 | 1/2004 | Kim et al. |
| 6,689,344 B2 | 2/2004 | Chang et al. |
| 6,705,541 B2 | 3/2004 | Schuehrer et al. |
| 6,730,316 B2 | 5/2004 | Chen |
| 6,732,887 B2 | 5/2004 | Bills et al. |
| 6,780,401 B2 | 8/2004 | Kim et al. |
| 6,949,240 B2 | 9/2005 | Sagel et al. |
| 6,956,142 B2 | 10/2005 | Bedekar et al. |
| 7,128,899 B2 | 10/2006 | Chen |
| 7,189,385 B2 | 3/2007 | Montgomery |
| 7,243,788 B2 | 7/2007 | Schmidt et al. |
| 7,510,859 B2 | 3/2009 | Wieland et al. |
| 7,552,823 B2 | 6/2009 | Schuehrer et al. |
| 7,723,083 B2 | 5/2010 | DiCosimo et al. |
| 7,754,460 B2 | 7/2010 | Amin et al. |
| 7,763,235 B2 | 7/2010 | Boyd et al. |
| 7,776,010 B2 | 8/2010 | Jessop et al. |
| 7,785,572 B2 | 8/2010 | Kim et al. |
| 7,794,378 B2 | 9/2010 | Splane et al. |
| 7,807,141 B2 | 10/2010 | Huang et al. |
| 7,829,315 B2 | 11/2010 | DiCosimo et al. |

(Continued)

FOREIGN PATENT DOCUMENTS

| WO | WO 92/017158 | 10/1992 |
| WO | WO 01/064175 | 9/2001 |

(Continued)

OTHER PUBLICATIONS

NCBI (National Center for Biotechnology Information. PubChem Compound Database; CID=31294, <https://pubchem.ncbi.nlm.nih.gov/compound/31294> (accessed Jun. 3, 2016)).*

International Search Report and Written Opinion in International Application No. PCT/US2011/051546, dated Jul. 16, 2012.

Nafee, 2004, "Mucoadhesive Delivery Systems. I. Evaluation of Mucoadhesive Polymers for Buccal Tablet Formulation," Drug Development and Industrial Pharmacy 30:985-993.

Shojaei et al., 2001, "Systemic Drug Delivery via the Buccal Mucosal Route," Pharmaceutical Technology pp. 70-81.

(Continued)

*Primary Examiner* — Nicole P Babson

(57) ABSTRACT

Described herein are tooth whitening strips comprising a hydratable adhesive film with a first side and a second side, the first side having a granular bleaching ingredient attached thereto in an amount effective to whiten teeth, together with methods of making and using the same.

11 Claims, No Drawings

(56) References Cited

U.S. PATENT DOCUMENTS

| | | |
|---|---|---|
| 7,862,801 B2 | 1/2011 | Chen |
| 7,862,802 B2 | 1/2011 | Kim et al. |
| 7,870,952 B2 | 1/2011 | Fontana et al. |
| 7,909,165 B2 | 3/2011 | Perrel et al. |
| 7,951,566 B2 | 5/2011 | DiCosimo et al. |
| 7,964,378 B2 | 6/2011 | DiCosimo et al. |
| 8,062,875 B2 | 11/2011 | DiCosimo et al. |
| 8,110,536 B2 | 2/2012 | Dietshe et al. |
| 8,206,964 B2 | 6/2012 | DiCosimo et al. |
| 8,222,012 B2 | 7/2012 | DiCosimo et al. |
| 8,252,562 B2 | 8/2012 | DiCosimo et al. |
| 8,354,381 B2 | 1/2013 | Fahnestock et al. |
| 8,518,675 B2 | 8/2013 | DiCosimo et al. |
| 8,663,616 B2 | 3/2014 | Butterick et al. |
| 2004/0018156 A1 | 1/2004 | Szeles et al. |
| 2004/0112769 A1 | 6/2004 | Perry et al. |
| 2005/0038181 A1 | 2/2005 | Chopra et al. |
| 2005/0063923 A1 | 3/2005 | Prencipe et al. |
| 2005/0069502 A1 | 3/2005 | Chopra et al. |
| 2005/0249678 A1 | 11/2005 | Hassan et al. |
| 2005/0253916 A1 | 11/2005 | Poncelet et al. |
| 2005/0260544 A1 | 11/2005 | Jones et al. |
| 2005/0287084 A1 | 12/2005 | Ibrahim et al. |
| 2006/0024246 A1 | 2/2006 | Maitra et al. |
| 2006/0292092 A1* | 12/2006 | Sharma et al. ............... 424/53 |
| 2006/0292520 A1 | 12/2006 | Dillon et al. |
| 2007/0128129 A1 | 6/2007 | Stehr et al. |
| 2007/0178055 A1 | 8/2007 | Buch et al. |
| 2007/0231277 A1 | 10/2007 | Sharma et al. |
| 2007/0269388 A1 | 11/2007 | Sagel et al. |
| 2008/0152600 A1 | 6/2008 | Huang et al. |
| 2008/0176299 A1 | 7/2008 | DiCosimo et al. |
| 2008/0176783 A1 | 7/2008 | DiCosimo et al. |
| 2008/0260836 A1 | 10/2008 | Boyd |
| 2009/0005590 A1 | 1/2009 | DiCosimo et al. |
| 2009/0311198 A1 | 12/2009 | Concar et al. |
| 2010/0041752 A1 | 2/2010 | DiCosimo et al. |
| 2010/0059394 A1 | 3/2010 | Fontana et al. |
| 2010/0086534 A1 | 4/2010 | DiCosimo et al. |
| 2010/0086535 A1 | 4/2010 | DiCosimo et al. |
| 2010/0087529 A1 | 4/2010 | DiCosimo et al. |
| 2010/0136639 A1 | 6/2010 | DiCosimo et al. |
| 2010/0196287 A1 | 8/2010 | O'Connell et al. |
| 2010/0247589 A1 | 9/2010 | Fahnestock et al. |
| 2011/0081693 A1 | 4/2011 | DiCosimo et al. |
| 2011/0236335 A1 | 9/2011 | DiCosimo et al. |
| 2011/0236339 A1 | 9/2011 | DiCosimo et al. |
| 2012/0288548 A1 | 11/2012 | Boyd et al. |
| 2012/0328534 A1* | 12/2012 | Butterick et al. ............ 424/50 |
| 2014/0105948 A1* | 4/2014 | Gebreselassie .......... A61K 8/11 424/401 |
| 2014/0314829 A1 | 10/2014 | Boyd et al. |
| 2015/0118167 A1 | 4/2015 | Boyd et al. |
| 2015/0265511 A1 | 9/2015 | Boyd et al. |

FOREIGN PATENT DOCUMENTS

| | | |
|---|---|---|
| WO | WO 02/074275 | 9/2002 |
| WO | WO 03/015656 | 2/2003 |
| WO | WO 04/024104 | 3/2004 |
| WO | WO 2004/028500 | 4/2004 |
| WO | WO 04/041102 | 5/2004 |
| WO | WO 05/056782 | 6/2005 |
| WO | WO 05/110344 | 11/2005 |
| WO | WO 2005/124012 | 12/2005 |
| WO | WO 2006/009737 | 1/2006 |
| WO | WO 06/069236 | 6/2006 |
| WO | WO 2006/111803 | 10/2006 |
| WO | WO 2007/041408 | 4/2007 |
| WO | WO 07/103050 | 9/2007 |
| WO | WO 08/140988 | 11/2008 |
| WO | WO 2009/015951 | 2/2009 |
| WO | WO 2010/039953 | 4/2010 |
| WO | WO 2011/041367 | 4/2011 |
| WO | WO 2011/090980 | 7/2011 |
| WO | WO 2011/094497 | 8/2011 |
| WO | WO 2012/087970 | 6/2012 |
| WO | WO 2013/039495 | 3/2013 |
| WO | WO 2013/096321 | 6/2013 |

OTHER PUBLICATIONS

Smart, 2004, "Recent developments in the use of bioadhesive systems for delivery of drugs to the oral cavity," Critical Reviews in Therapeutic Drug Carrier Systems 21:319-344.

Sudhakar et al., 2006, "Buccal bioadhesive drug delivery—a promising option for orally less efficient drugs," J. Controlled Release 114(1):15-40.

Written Opinion in International Application No. PCT/US2011/051546, dated Aug. 20, 2013.

Altschul et al., 1990, "Basic Local Alignment Search Tool," J. Mol. Biol. 215, p. 403-410.

Binz et al., 2005, "Engineering novel binding proteins from nonimmunoglobulin domains," Nature Biotechnology 23(10), p. 1257-1268.

Chenna et al., 2003, "Multiple sequence alignment with the Clustal series of programs," Nucleic Acids Res 31(13), p. 3497-3500.

Coutinho et al., 1999, "Carbohydrate-active enzymes: an integrated database approach" in Recent Advances in Carbohydrate Bioengineering, Gilbert et al., eds., The Royal Society of Chemistry, Cambridge, p. 3-12.

Dinu et. al. 2010, "Enzyme-based nanoscale composites for use as active decontamination surfaces," Adv. Funct. Materials 20, p. 392-398.

Dong et al., 2007, "Cosmetics Formulation Design and Production Process 1st Edition" China Textile & Apparel Press, p. 79-80.

Grachyova, 1987, Tekhonologiya fermentnyhk preparatov, 2nd Issue, revised, M.: Agropromizdat, p. 149.

Goujon et al., 2010, "A new bioinformatics analysis tools framework at EMBL-EBI," Nucleic Acids Research, 38(Suppl), p. W695-699.

Higgins et al., 1989, "Fast and sensitive multiple sequence alignments on a microcomputer," CABIOS Communications, 5(2), p. 151-153.

Hosse et al., 2006, "A new generation of protein display scaffolds for molecular recognition," Protein Science 15(1), p. 14-27.

International Search Report of International Application PCT/US2011/65827, dated Nov. 22, 2012.

International Search Report in International Application PCT/US2012/070371, dated Feb. 13, 2014, 5 pages.

International Search Report in International Application PCT/US2012/070367, dated Feb. 13, 2014, 5 pages.

Mitsushima et al., 1995, "Gene cloning, nucleotide sequence, and expression of a cephalosporin-C Deacetylase from Bacillus subtilis," Appl. Env. Microbiol., 61(6), p. 2224-2229.

Muyldermans, 2001, "Single domain camel antibodies: current status," Reviews in Molecular Biotechnol., 74, p. 277-302.

Needleman et al., 1970, "A general method applicable to the search for similarities in the amino acid sequence of two proteins," J. Mol. Biol. 48, p. 443-453.

Pearson, 1994, "Searching protein sequence databases—is optimal best?" Computational Methods in Genome Research, [Proc. Int. Symp.], p. 111-120.

Pinkernell et al., 1997, "Simultaneous HPLC Determination of peroxyacetic acid and hydrogen peroxide," Analytical Chem. 69(17), p. 3623-3627.

Pinkernell et. al., 1997, "Sepective photometric determination of peroxycarboxylic acids in the presence of hydrogen peroxide," Analyst, 122, p. 567-571.

Prokhorov, 1972 Bolshaya Sovetskaya Entsiklopediya, 3rd Issue, vol. 7, M.: Sov. Entisiklopediya, p. 254.

Rice et al., 2000, "EMBOSS: The European molecular biology open software suite," Trends in Genetics 16(6), p. 276-277.

Smith-Waterman, 1981, "Identification of common molecular subsequences," J. Mol. Biol., 147, p. 195-197.

STN Chemical Abstracts Registry Database, 1984, CAS Registry No. 25395-31-7.

(56) References Cited

OTHER PUBLICATIONS

STN Chemical Abstracts Registry Database, 1984, CAS Registry No. 102-76-1.
STN Chemical Abstracts Registry Database, 1984, CAS Registry No. 623-84-7.
STN Chemical Abstracts Registry Database, 1984, CAS Registry No. 111-55-7.
Thompson et al., 1994, "CLUSTAL W: Improving the sensitivity of progressive multiple sequence alignment through sequence weighting, position-specific gap penalties and weight matrix choice," Nucleic Acids Research, 22(22), p. 4673-4680.
Vincent et al., 2003, "Multifunctional xylooligosaccharide/cephalosporin C deacetylase revealed by the hexameric structure of the bacillus subtilis enzyme at 1.9 Å Resolution," J. Mol. Biol. 330, p. 593-606.

* cited by examiner

TOOTH WHITENING STRIP

BACKGROUND

There exists a need for whitening strips suitable for home use, having reduced total levels of peroxide, yet providing enhanced whitening activity.

SUMMARY

Some embodiments of the present invention provide whitening strips that deliver a solid peroxide material directly to the teeth, without substantial dilution from formulation excipients, thereby permitting enhanced bleaching with lower total amounts of peroxide. In some embodiments, the strips comprise an adhesive film, which hydrates in water or saliva to stick to teeth. In further embodiments, the strip is applied in such a way to ensure that the bleaching ingredient is placed directly on the teeth (that is, between the teeth and the adhesive layer), permitting the granules to release peroxide by rapidly dissolving in oral cavity environment. The bleaching ingredient can be optionally coated by or incorporated within a matrix comprising a quickly dissolving material, such as hydroxypropylmethyl cellulose, cornstarch or gum arabic.

In some embodiments, the strip further comprises a perhydrolase (e.g., an enzyme capable of catalyzing the reaction of carboxylic acid and hydrogen peroxide to form a peracid) and a carboxyl donor, e.g., selected from carboxylic acids and acyl compounds, wherein the carboxyl donor reacts with the peroxide source in the strip in the presence of the perhydrolase to form a peracid, which further enhances the bleaching action of the strip. In yet other embodiments, the strips comprise a peroxygen compound in granular form and an orally acceptable ketone which react to provide a dioxirane, thereby enhancing the bleaching action of the strip.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

DETAILED DESCRIPTION

As used throughout, ranges are used as shorthand for describing each and every value that is within the range. Any value within the range can be selected as the terminus of the range.

All references cited herein are hereby incorporated by reference in their entireties.

In the event of a conflict in a definition in the present disclosure and that of a cited reference, the present disclosure controls.

Exemplary embodiments of the invention include for example tooth whitening strips and methods of whitening teeth, e.g.:

1. A tooth whitening strip (Strip 1) comprising a hydratable adhesive film with a first side and a second side, the first side having a granular bleaching ingredient attached thereto in an amount effective to whiten teeth; for example,
    1.1. Strip 1 further comprising a backing layer. In some embodiments, the backing layer controls dissolution of the hydratable adhesive film.
    1.2. Strip 1 or 1.1 wherein the granular bleaching ingredient is coated with or incorporated within a matrix comprising a quickly dissolving material, e.g., cornstarch or gum arabic. In some embodiments, the matrix dissolves more quickly than the hydratable adhesive film. In some embodiments, the matrix dissolves at a rate substantially similar to the dissolution rate of the hydratable adhesive film.
    1.3. Any of the foregoing strips wherein the granular bleaching ingredient is selected from solid peroxides and solid peroxide donors, e.g., selected from peroxide salts or complexes (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, sodium peroxydisulphate, and potassium persulfate); hypochlorites; urea peroxide; hydrogen peroxide polymer complexes such as hydrogen peroxide-polyvinyl pyrrolidone polymer complexes; metal peroxides e.g. zinc peroxide and calcium peroxide; peracids, e.g., 6-phthalimodoperoxyhexanoic acid (P.A.P.); and combinations thereof.
    1.4. Any of the foregoing strips wherein the granular bleaching ingredient comprises urea peroxide.
    1.5. Any of the foregoing strips where the particle size (D50) of the granular bleaching ingredient is from about 10 to about 500 microns, e.g. from about 60 to about 150 microns. In some embodiments, the particle size (D50) of the granular bleaching ingredient is from about 15 to about 450 microns. In some embodiments, the particle size (D50) of the granular bleaching ingredient is from about 20 to about 400 microns. In some embodiments, the particle size (D50) of the granular bleaching ingredient is from about 25 to about 350 microns. In some embodiments, the particle size (D50) of the granular bleaching ingredient is from about 30 to about 300 microns. In some embodiments, the particle size (D50) of the granular bleaching ingredient is from about 35 to about 250 microns. In some embodiments, the particle size (D50) of the granular bleaching ingredient is from about 40 to about 225 microns. In some embodiments, the particle size (D50) of the granular bleaching ingredient is from about 45 to about 200 microns. In some embodiments, the particle size (D50) of the granular bleaching ingredient is from about 50 to about 175 microns. In some embodiments, the particle size (D50) of the granular bleaching ingredient is from about 55 to about 160 microns. In some embodiments, the particle size (D50) of the granular bleaching ingredient is from about 65 to about 145 microns. In some embodiments, the particle size (D50) of the granular bleaching ingredient is from about 70 to about 140 microns. In some embodiments, the particle size (D50) of the granular bleaching ingredient is from about 75 to about 135 microns. In some embodiments, the particle size (D50) of the granular bleaching ingredient is from about 80 to about 125 microns. In some embodiments, the particle size (D50) of the granular bleaching ingredient is from about 85 to about 120 microns. In some embodiments, the particle size (D50) of the granular bleaching ingredient is from about 90 to about 110 microns. In some embodiments, the particle size (D50) of the granular bleaching ingredient is from about 95 to about 100 microns.
    1.6. Any of the foregoing strips wherein the granular bleaching ingredient comprises about 1.0% or less, e.g. from about 0.01 to about 1.0%, e.g. from about 0.2 to about 0.8%, of the total weight of the hydratable adhesive film and a granular bleaching ingredient attached thereto.

1.7. Any of the foregoing strips wherein the granular bleaching ingredient comprises about 0.1% or less, e.g. from about 0.01 to about 0.1%, e.g. from about 0.02 to about 0.08%, of the total weight of the hydratable adhesive film and a granular bleaching ingredient attached thereto.

1.8. Any of the foregoing strips wherein the amount of granular bleaching agent on the first side of the hydratable adhesive film is from about 0.001 to about 1 mg/cm$^2$, e.g., from about 0.001 to about 0.1 mg/cm$^2$, for example from about 0.005 to about 0.015 mg/cm$^2$.

1.9. In some embodiments, the amount of granular bleaching agent on the first side of the hydratable adhesive film is from about 0.01 to about 0.75 mg/cm$^2$. In some embodiments, the amount of granular bleaching agent on the first side of the hydratable adhesive film is from about 0.05 to about 0.7 mg/cm$^2$. In some embodiments, the amount of granular bleaching agent on the first side of the hydratable adhesive film is from about 0.075 to about 0.65 mg/cm$^2$. In some embodiments, the amount of granular bleaching agent on the first side of the hydratable adhesive film is from about 0.1 to about 0.6 mg/cm$^2$. In some embodiments, the amount of granular bleaching agent on the first side of the hydratable adhesive film is from about 0.15 to about 0.55 mg/cm$^2$. In some embodiments, the amount of granular bleaching agent on the first side of the hydratable adhesive film is from about 0.2 to about 0.5 mg/cm$^2$. In some embodiments, the amount of granular bleaching agent on the first side of the hydratable adhesive film is from about 0.25 to about 0.45 mg/cm$^2$. In some embodiments, the amount of granular bleaching agent on the first side of the hydratable adhesive film is from about 0.3 to about 0.4 mg/cm$^2$.

1.10. In some embodiments, the amount of granular bleaching agent on the first side of the hydratable adhesive film is from about 0.005 to about 0.1 mg/cm$^2$. In some embodiments, the amount of granular bleaching agent on the first side of the hydratable adhesive film is from about 0.0075 to about 0.095 mg/cm$^2$. In some embodiments, the amount of granular bleaching agent on the first side of the hydratable adhesive film is from about 0.01 to about 0.09 mg/cm$^2$. In some embodiments, the amount of granular bleaching agent on the first side of the hydratable adhesive film is from about 0.015 to about 0.085 mg/cm$^2$. In some embodiments, the amount of granular bleaching agent on the first side of the hydratable adhesive film is from about 0.02 to about 0.08 mg/cm$^2$. In some embodiments, the amount of granular bleaching agent on the first side of the hydratable adhesive film is from about 0.025 to about 0.08 mg/cm$^2$. In some embodiments, the amount of granular bleaching agent on the first side of the hydratable adhesive film is from about 0.03 to about 0.08 mg/cm$^2$. In some embodiments, the amount of granular bleaching agent on the first side of the hydratable adhesive film is from about 0.035 to about 0.08 mg/cm$^2$. In some embodiments, the amount of granular bleaching agent on the first side of the hydratable adhesive film is from about 0.04 to about 0.08 mg/cm$^2$. In some embodiments, the amount of granular bleaching agent on the first side of the hydratable adhesive film is from about 0.045 to about 0.08 mg/cm$^2$. In some embodiments, the amount of granular bleaching agent on the first side of the hydratable adhesive film is from about 0.05 to about 0.08 mg/cm$^2$. In some embodiments, the amount of granular bleaching agent on the first side of the hydratable adhesive film is from about 0.055 to about 0.08 mg/cm$^2$. In some embodiments, the amount of granular bleaching agent on the first side of the hydratable adhesive film is from about 0.06 to about 0.08 mg/cm$^2$. In some embodiments, the amount of granular bleaching agent on the first side of the hydratable adhesive film is from about 0.065 to about 0.08 mg/cm$^2$. In some embodiments, the amount of granular bleaching agent on the first side of the hydratable adhesive film is from about 0.07 to about 0.08 mg/cm$^2$.

1.11. In some embodiments, the amount of granular bleaching agent on the first side of the hydratable adhesive film is from about 0.075 to about 0.08 mg/cm$^2$. In some embodiments, the amount of granular bleaching agent on the first side of the hydratable adhesive film is about 0.078 mg/cm$^2$.

1.12. In some embodiments, the amount of granular bleaching agent on the first side of the hydratable adhesive film is from about 0.005 to about 0.25 mg/cm$^2$. In some embodiments, the amount of granular bleaching agent on the first side of the hydratable adhesive film is from about 0.005 to about 0.1 mg/cm$^2$. In some embodiments, the amount of granular bleaching agent on the first side of the hydratable adhesive film is from about 0.005 to about 0.075 mg/cm$^2$. In some embodiments, the amount of granular bleaching agent on the first side of the hydratable adhesive film is from about 0.005 to about 0.05 mg/cm$^2$. In some embodiments, the amount of granular bleaching agent on the first side of the hydratable adhesive film is from about 0.0075 to about 0.04 mg/cm$^2$. In some embodiments, the amount of granular bleaching agent on the first side of the hydratable adhesive film is from about 0.009 to about 0.035 mg/cm$^2$. In some embodiments, the amount of granular bleaching agent on the first side of the hydratable adhesive film is from about 0.01 to about 0.03 mg/cm$^2$. In some embodiments, the amount of granular bleaching agent on the first side of the hydratable adhesive film is from about 0.01 to about 0.025 mg/cm$^2$. In some embodiments, the amount of granular bleaching agent on the first side of the hydratable adhesive film is from about 0.01 to about 0.02 mg/cm$^2$.

1.13. Any of the foregoing strips further comprising (i) a perhydrolase (e.g., an enzyme capable of catalyzing the reaction of carboxylic acid and hydrogen peroxide to form a peracid), for example, a perhydrolase comprising a Ser-His-Asp catalytic triad, e.g., derived from a lipase, serine hydrolase or carbohydrate esterase, and (ii) a carboxyl donor, e.g., selected from carboxylic acids and acyl compounds, wherein upon use, the peroxide released by the granular bleaching ingredient reacts with the carboxyl donor in the presence of the perhydrolase to form a peracid.

1.14. The foregoing strip wherein the carboxyl donor is selected from (i) one or more $C_{2-18}$ carboxylic acids, e.g $C_{2-6}$ carboxylic acids (e.g., acetic acid), including lower linear or branched alkyl carboxylic acids, optionally substituted with hydroxyl and/or $C_{1-4}$ alkoxyl; (ii) one or more hydrolysable and acceptable esters thereof (e.g. mono-, di-, and tri-glycerides and acylated saccharides) and (iii) mixtures thereof.

1.15. The foregoing strip wherein the carboxyl donor is selected from 1,2,3-triacetoxypropane (sometimes referred to herein as triacetin or glycerin triacetate) and acylated saccharides, e.g. acetylated saccharides.

1.16. Any of the foregoing strips comprising a carboxyl donor which comprises an ester compound having solubility in water of at least 5 ppm at 25° C.

1.17. Any of the foregoing strips comprising an orally acceptable ketone, e.g., a $C_{3-8}$ alkyl ketone compound, for example methyl ethyl ketone, wherein the ketone is oxidized to the corresponding dioxirane when the strip is used.

1.18. Any of the foregoing strips which comprise a peracid or which generates a peracid upon use, e.g., wherein the peracid is selected from peracetic acid or phthalimidoperoxyhexanoic acid (P.A.P.).

1.19. Any of the foregoing strips wherein the ingredients are present in amounts sufficient to provide, upon mixing, a bleaching agent in an amount and concentration effective to whiten teeth.

1.20. Any of the foregoing strips wherein the hydratable adhesive film comprises one or more water-soluble polymers selected from hydrophilic cellulose ethers (e.g. carboxymethyl cellulose, hydroxypropyl cellulose, hydroxypropyl methylcellulose,), polyvinyl acetates, carbomers (e.g., Carbopol 971P), polysaccharide gums (e.g. xanthan gum), modified food starches, gelatin (e.g. animal or fish-based gelatin), cross-linked carboxyvinyl copolymers, cross-linked polyvinylpyrrolidones, polyethylene oxide (ak.a. Polyox), polyacrylic acids and polyacrylates, polyvinyl alcohols, alginate, casein, pullulan, and combinations thereof.

1.21. Any of the foregoing strips wherein the hydratable adhesive film comprises one or more water-soluble polymers selected from hydrophilic cellulose ethers (e.g. hydroxypropylmethyl cellulose), polyvinyl acetates, and carbomers (e.g., Carbopol 971P), and combinations thereof.

1.22. Any of the foregoing strips wherein the hydratable adhesive film comprises hydroxypropylmethyl cellulose, polyvinyl acetates, and a carbomer, e.g., in a dry weight ratio of 10 to 20 HPMC:2 to 10 PVAc:1 carbomer.

1.23. Any of the foregoing strips wherein the hydratable adhesive film further comprises a plasticizer, e.g. propylene glycol.

1.24. Any of the foregoing strips wherein the first side of the hydratable adhesive film is covered by a protective cover prior to use.

1.25. Any of the foregoing strips wherein the hydratable adhesive film is substantially dry prior to application.

1.26. Any of the foregoing strips wherein the thickness of the hydratable adhesive film is from about 0.5 to about 15 mil, wherein 1 mil=0.001 inches.

1.27. Any of the foregoing strips wherein the approximate overall dimensions are from about 3 to about 9 cm long×from about 0.5 to about 2.5 cm wide×from about 0.5 to about 15 mil thick, for example a strip wherein the surface area of one side is from about 5 to about 15 $cm^2$, e.g., from about 10 to about 12 $cm^2$.

1.28. Any of the foregoing strips wherein the approximate overall dimensions are from about 5 to about 7 cm long×from about 1.5 to about 2.5 cm wide×from about 2 to about 7 mil thick, for example a strip wherein the surface area of one side is from about 7.5 to about 16 $cm^2$, e.g., from about 10 to about 12 $cm^2$.

2. Some embodiments of the present invention provide a method of whitening teeth comprising applying the first side of a strip as hereinbefore described, e.g. Strip 1 et seq. directly to the teeth, and leaving it on for a sufficient time, e.g., at least 5 minutes, for example 10-30 minutes, to whiten the teeth.

3. Other embodiments provide a method of making a strip for tooth whitening, e.g., a strip as hereinbefore described, according to Strip 1 et seq., comprising providing a semi-dry hydratable adhesive film, e.g., as hereinbefore described, e.g., which film has been cast from water and not fully dried, or which film has been moistened, adding to one surface of the film granules of a granular bleaching ingredient, e.g., as hereinbefore described, and drying the film with the granules added to one surface.

For example, the strips may be made by first making the hydratable adhesive film using conventional means, then adding the granulated whitening ingredient to one surface. The hydratable adhesive film strips can be cast from water in a variety of ways known in the art, such as by extrusion, or by casting from a water suspension (for example at a solids level of 10-30%) onto a heated belt, from which the water is evaporated. Alternatively, the film is dried, but then remoistened. The granules can be added to the surface of this film while the film is semi-dry, i.e. just moist enough to be tacky, so that the granules stick to the surface of the film. Alternatively, the granules themselves can be moistened to improve adhesion, either as the primary means or in conjunction with one of the aforementioned approaches. Once the film is fully dry and cooled to room temperature, the granules continue to adhere to the surface of the film. Prior to use, therefore, the hydratable adhesive film and the strip as a whole are substantially dry. Because the peroxide is on the surface of the film only, a relatively small quantity of granules are required to provide an effective concentration at the surface. For 0.1% hydrogen peroxide equivalent in the single layer strip, a base film with a surface area of 10 $cm^2$ and a dry weight of 7.75 $mg/cm^2$ would require only about 0.078 mg of bleach granules.

When exposed to saliva or other sources of water (such as from a sink), the granules become active. The hydratable adhesive film also is activated and sticks to the teeth effectively.

In some embodiments, the hydratable adhesive film comprises one or more water-soluble, orally acceptable polymers, e.g. selected from hydrophilic cellulose ethers (e.g. carboxymethyl cellulose, hydroxypropyl cellulose, hydroxypropyl methylcellulose,), polyvinyl acetates, carbomers (e.g., Carbopol 971P), polysaccharide gums (e.g. xanthan gum), modified food starches, gelatin (e.g. animal or fish-based gelatin), cross-linked carboxyvinyl copolymers, cross-linked polyvinylpyrrolidones, polyethylene oxide (ak.a. Polyox), polyacrylic acids and polyacrylates, polyvinyl alcohols, alginate, casein, pullulan, and combinations thereof. Adhesive gel formulations for use with tooth whitening agents are known in the art, e.g. as described in U.S. Pat. Nos. 7,862,801; 5,746,598; 6,730,316; 7,128,899. The hydratable adhesive film allows the bleaching agent to stay in contact with the teeth for extended periods of time and protects soft tissues.

Where a second film layer (e.g. carrier or backing layer) is used to protect the hydratable adhesive film from rapid degradation or dissolution, the carrier or backing layer may be made from textiles, cloth, wood composite, resin, elastomer, paper, insoluble or less soluble cellulose derivatives such as ethyl cellulose and cellulose acetate, polyvinyl chloride, wax, Parafilms™, polyethylene, polyvinyl alcohol, Teflon™, polyvinyl chloride, polyvinyl acetate and their derivatives.

The granular bleaching ingredient may be a solid peroxide or solid peroxide donor or other active oxygen donor, e.g., selected from peroxide salts or complexes (e.g., such as peroxyphosphate, peroxycarbonate, perborate, peroxysilicate, peroxymonosulphate or peroxydisulphate salts; for example calcium peroxyphosphate, sodium perborate, sodium carbonate peroxide, sodium peroxyphosphate, sodium peroxydisulphate, and potassium persulfate), hypochlorites; urea peroxide; hydrogen peroxide polymer complexes such as hydrogen peroxide-polyvinyl pyrrolidone polymer complexes, and metal peroxides e.g. zinc peroxide and calcium peroxide; a solid peracid, e.g., phthalimidoperoxyhexanoic acid (P.A.P.); and combinations thereof. In particular embodiments, the granular bleaching ingredient is urea peroxide.

Peroxycarboxylic acids ("peracids") useful in the present invention are known as effective antimicrobial and bleaching agents. U.S. Pat. No. 5,302,375 to Viscio, D., discloses oral compositions for whitening comprising peracetic acid dissolved in a vehicle, wherein the peracetic acid is generated within the vehicle in situ by combining water, acetylsalicylic acid, and a water soluble alkali metal percarbonate. U.S. Pat. No. 5,279,816 to Church et al. discloses the use of a composition comprising peracetic acid to whiten stained or discolored teeth. U.S. Pat. Nos. 6,221,341 and 7,189,385 to Montgomery, R., disclose peroxy acid tooth-whitening compositions suitable for use in a method to whiten teeth. More specifically, a peracetic acid composition may be produced by combining a hydrogen peroxide precursor, an acetic acid ester of glycerin, and water to generate, via chemical perhydrolysis, peracetic acid. Perhydrolase enzymes are also reported, for example, in WO 2005/056782.

Many hydrolases and esterases, for example, lipases, serine hydrolases and carbohydrate esterases, catalyze perhydrolysis, the reversible formation of peracids from carboxylic acids and hydrogen peroxide. Perhydrolases, esterases, and lipases generally contain a catalytic triad consisting of a serine (Ser), a glutamate (Glu) or aspartate (Asp), and a histidine (His). Many perhydrolases (e.g. metal-free haloperoxidases) contain a Ser-His-Asp catalytic triad and catalyze the reversible formation of peracid from hydrogen peroxide and carboxylic acids. Without being bound by theory, it is believed that perhydrolysis takes place with an esterase-like mechanism in which a carboxylic acid reacts with the active site serine to form an acyl enzyme intermediate, which then reacts with hydrogen peroxide to form a peracid.

Numerous perhydrolases have been described in the art. The inclusion of specific variant subtilisin Carlsberg proteases having perhydrolytic activity in a body care product is disclosed in U.S. Pat. No. 7,510,859 to Wieland et al. Perhydrolytic enzymes beyond the specific variant proteases are not described nor are there any working examples demonstrating the enzymatic production of peracid as a personal care benefit agent.

Carboxyl donors for use in the present invention, e.g., to form peracids upon reaction with peroxide, are selected from one or more of (i) $C_{2-18}$ carboxylic acids, e.g $C_{2-6}$ carboxylic acids (e.g., acetic acid), including lower linear or branched alkyl carboxylic acids, optionally substituted with hydroxyl and/or $C_{1-4}$ alkoxyl; (ii) hydrolysable and acceptable esters thereof (e.g. mono-, di-, and tri-glycerides and acylated saccharides) and (iii) mixtures thereof. For example, carboxyl donors include 1,2,3-triacetoxypropane (sometimes referred to herein as triacetin or glycerin triacetate) and acylated saccharides, e.g. acetylated saccharides. In a particular embodiment, esters for this use may, for example, be esters having solubility in water of at least 5 ppm at 25° C.

The carboxyl donors and/or enzymes may optionally be encapsulated. There are a variety of encapsulation options well-known to the art, both natural and synthetic. Modified celluloses, modified starches and gum arabic are particularly well-suited since they are food grade, relatively inexpensive, quick to dissolve, and can adsorb fairly high levels of liquid oils.

All ingredients for use in the strips described herein should be orally acceptable. By "orally acceptable" as the term is used herein is meant an ingredient which is present in a strip as described in an amount and form which does not render the strip unsafe for use in the oral cavity.

Unless otherwise specified, all percentages and amounts expressed herein and elsewhere in the specification should be understood to refer to percentages by weight. The amounts given are based on the active weight of the material.

EXAMPLES

Example 1

A strip is prepared as described above, forming the hydratable adhesive film and then while the film is still tacky, adding the granulated whitening agent to the surface of one side, using the ingredients in Table 1. The strip will erode slowly in the mouth upon application, and so does not need to be removed.

TABLE 1

| Ingredients in film | Weight % of dry film |
|---|---|
| Hydroxypropylmethylcellulose (HPMC) | 59 |
| Polyvinyl acetate (PVAc) | 30 |
| Carbomer (CARBOPOL ® 971) | 5 |
| Propylene glycol | 5 |
| Titanium dioxide | 1 |
| Total | 100 |

| Ingredients in bleach granules | Concentration (%) |
|---|---|
| Urea peroxide | 100 |

Example 2

A strip is prepared as described above, forming the hydratable adhesive film and then while the strip is still tacky, adding the granulated whitening agent to one side and the protective backing layer to the other side, using the ingredients in Table 2. Because the backing layer will not dissolve, the user should remove it after a sufficient period has passed to permit whitening to take place, typically about 10-30 minutes. The two layers can also be produced simultaneously by extrusion or solvent-based casting, then the granulated whitening agent can be added to the surface of the hydratable adhesive film.

TABLE 2

| Ingredients in backing layer | Weight % of dry strip |
|---|---|
| Ethyl cellulose | 94 |
| Propylene glycol | 5 |
| Titanium dioxide | 1 |

TABLE 2-continued

| Ingredients in hydratable adhesive strip | Weight % of dry strip |
| --- | --- |
| Hydroxypropylmethylcellulose (HPMC) | 69 |
| Polyvinyl acetate (PVAc) | 15 |
| Carbomer (CARBOPOL ® 971) | 5 |
| Propylene glycol | 5 |
| Titanium dioxide | 1 |
| Total | 100 |

| Ingredients in bleach granules | Concentration (%) |
| --- | --- |
| Urea peroxide | 100 |

As those skilled in the art will appreciate, numerous changes and modifications may be made to the embodiments described herein without departing from the spirit of the invention. It is intended that all such variations fall within the scope of the appended claims.

What is claimed is:

1. A tooth whitening strip comprising a hydratable adhesive film with a first side and a second side, the first side having a granular bleaching ingredient attached thereto in an amount effective to whiten teeth, wherein the granular bleaching ingredient is attached to a surface of the film, wherein the tooth whitening strip further comprises a backing layer, wherein the backing layer controls dissolution of the hydratable adhesive film; and wherein the whitening strip further comprises
    (i) a perhydrolase
    (ii) a carboxyl donor, wherein the carboxyl donor is 1,2,3-triacetoxypropane; and
    wherein upon use, peroxide released by the granular bleaching ingredient reacts with the carboxyl donor in the presence of the perhydrolase to form a peracid; and
    wherein the hydratable adhesive film comprises hydroxypropylmethyl cellulose (HPMC), polyvinyl acetates (PVAc), and a carbomer in a dry weight ratio for HMPC:PVAc:carbomer of 10-20:20-10:1;
    wherein the granular bleaching ingredient comprises from 0.01 to 0.1% of the total weight of the hydratable adhesive film and the granular bleaching ingredient attached thereto; and wherein the particle size (D50) of the granular bleaching ingredient is from about 10 to about 500 microns.

2. The tooth whitening strip of claim 1, wherein the granular bleaching ingredient is coated with or incorporated within a matrix comprising a quickly dissolving material.

3. The tooth whitening strip of claim 1, wherein the granular bleaching ingredient is selected from solid peroxides, solid peroxide donors, and solid oxygen donors.

4. The tooth whitening strip of claim 1, wherein the granular bleaching ingredient is selected from peroxide salts or complexes, peroxyphosphate, peroxycarbonate, perborate, peroxysilicate, persulphate salts, calcium peroxyphosphate, sodium perborate, sodium carbonate peroxide, sodium peroxyphosphate, sodium peroxydisulphate, potassium persulfate, hypochlorites, urea peroxide, hydrogen peroxide polymer complexes, hydrogen peroxide-polyvinyl pyrrolidone polymer complexes, metal peroxides, zinc peroxide, calcium peroxide, peracids, phthalimidoperoxyhexanoic acid (P.A.P.), and combinations thereof.

5. The tooth whitening strip of claim 1, wherein the granular bleaching ingredient comprises urea peroxide.

6. The tooth whitening strip of claim 1, wherein the granular bleaching ingredient comprises from 0.02 to 0.08% of the total weight of the hydratable adhesive film and a granular bleaching ingredient attached thereto.

7. The tooth whitening strip of claim 1, wherein the amount of granular bleaching agent on the first side of the hydratable adhesive film is from about 0.001 to about 1 mg/cm$^2$.

8. The tooth whitening strip of claim 1, further comprising an orally acceptable ketone, wherein the ketone is oxidized to the corresponding dioxirane when the strip is used.

9. The tooth whitening strip of claim 1, wherein the ingredients are present in amounts sufficient to provide, upon mixing, a bleaching agent in an amount and concentration effective to whiten teeth.

10. The tooth whitening strip of claim 1, wherein the hydratable adhesive film further comprises a plasticizer.

11. The tooth whitening strip of claim 1, further comprising propylene glycol.

\* \* \* \* \*